United States Patent [19]
Ghaly

[11] Patent Number: 4,649,908
[45] Date of Patent: Mar. 17, 1987

[54] EYE SHIELD

[76] Inventor: Maurice S. Ghaly, Woodside Rd., P.O. Box 3324, Brunswick, Me. 04011

[21] Appl. No.: 707,136

[22] Filed: Mar. 1, 1985

[51] Int. Cl.$^4$ .............................................. A61F 9/04
[52] U.S. Cl. .................................... 128/132 R; 2/15
[58] Field of Search ............ 128/132 R, 132 D; 2/12, 2/15, 427, 428, 431, 440, 454; 351/41; D24/66; 604/301, 308; 446/220

[56] References Cited

U.S. PATENT DOCUMENTS

| 850,997 | 4/1907 | Cover | 2/440 |
|---|---|---|---|
| 1,886,725 | 11/1932 | Pedersen | 604/308 |
| 2,572,638 | 10/1951 | Loos | 128/163 |
| 3,619,815 | 11/1971 | Towner, Jr. | 128/132 R X |
| 4,019,516 | 4/1977 | D'Auria | 604/308 |
| 4,122,847 | 10/1978 | Craig | 128/132 R |
| 4,411,263 | 10/1983 | Cook | 128/132 R |
| 4,502,476 | 3/1985 | Welt | 128/132 R |

FOREIGN PATENT DOCUMENTS

| 2379302 | 9/1978 | France | 446/220 |
|---|---|---|---|
| 2123297 | 2/1984 | United Kingdom | 128/132 D |

Primary Examiner—Richard T. Stouffer
Attorney, Agent, or Firm—Daniel H. Kane, Jr.

[57] ABSTRACT

An eye shield device protects one or both eyes of an individual during medical treatment, or while the individual is comatose, semi-comatose, or under anesthesia. The eye shield includes at least one soft, pliable air-filled cushion member of thin plastic material, sized and shaped to fit within the cavity formed by the orbital bone structure around the eye. During use, the cushion member is placed upon the closed eye and is secured in place by the eye shield support removably affixed to the head of the individual. The cushion member or eye pillow is formed with a pleated side edge for expansion of the air in a "bellows" effect at the periphery to redistribute pressure on the eye to the perimeter and reduce direct pressure on the eye globe. The cushion member is also formed with a central cavity on the side placed upon the closed eye to accommodate the curvature of the eye ball. An adhesive layer may be placed on the cushion member for contact with the upper eyelid of the closed eye, to assist in holding the eyelid closed and in securing the cushion member in place.

6 Claims, 8 Drawing Figures

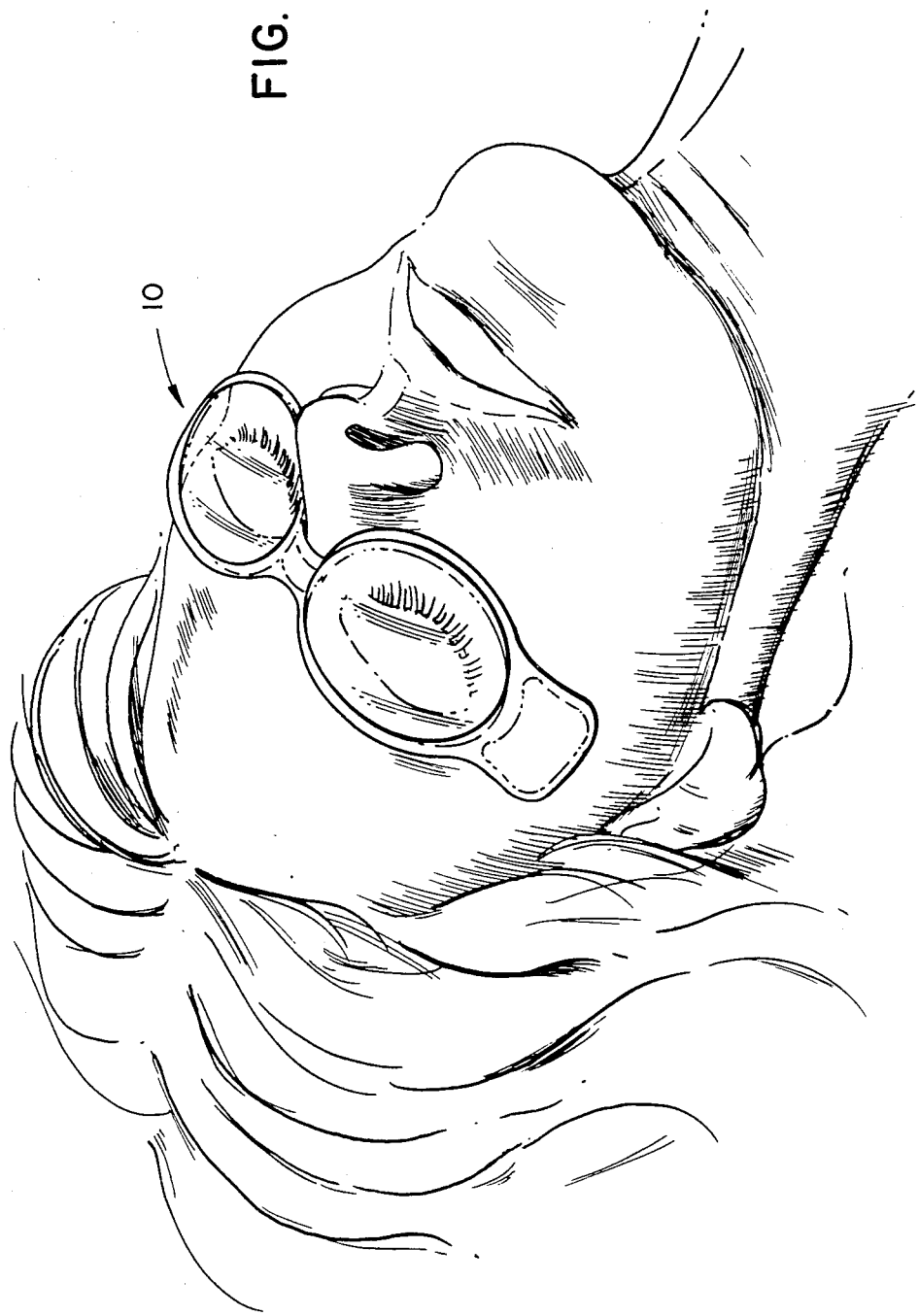

ically on each of the upper eyelids when closed. This
EYE SHIELD

TECHNICAL FIELD

This invention relates to an eye shield device, and particularly to an eye shield for use in protecting the eyes of a patient who is comatose, semi-comatose, under general anesthesia, and/or undergoing medical treatment.

BACKGROUND ART

The protection of the eyes of a patient who is comatose, semi-comatose, or under anesthesia, or is undergoing medical treatment, is of vital importance. All too often, a patient sustains an eye injury as a result of the various medical devices and instruments used near the head, or due to the dropping of foreign matter onto the eye. The risk of injury is, of course, greatest when the eye is not completely closed. Many methods and devices have been employed in an attempt to protect the eyes during such period of treatment and/or unconsciousness. For example, physicians often employ fabric or gauze eye pads such as described in U.S. Pat. Nos. 4,019,516 and 2,572,638. Such pads are held in place upon the eye by ordinary cloth adhesive tape or by an eye mask such as described in U.S. Pat. Nos. 4,019,516 and 1,886,725. However, the cotton wool gauze pads are collapsed easily by pressure.

Such conventional methods require several steps in positioning the eye pads in place, and then in taping them or otherwise applying them to the patient. In another method, a small strip of tape is placed horizontally on each of the upper eyelids when closed. This latter method is not wholly satisfactory, however, because it requires an accurate trimming of the strip of tape and placement of the tape strips as close to the lid margins as possible. There is an increased risk of eye injury in attempting such an accurate placement.

A rigid cover device or goggle-like device on the other hand such as described in U.S. Pat. No. 4,122,847 has the potential for breaking and injuring the eye. This most likely will occur if the patient is positioned in the face prone position.

OBJECTS OF THE INVENTION

An object of the present invention is to provide a simple, inexpensive, reliable, and preferably disposable eye shield device that is easily applied to an individual and will protect the cornea and conjunctiva of one or both eyes of a patient. Another object of the invention is to provide an eye shield and cushion which sustains sufficient pressure and affords greater pliability than conventional gauze or fabric pads. By the eye shield device of the present invention, the eyelid is gently held in a closed position, and at the same time is protected by soft cushioning from injury during treatment of the patient.

DISCLOSURE OF THE INVENTION

To accomplish these results, the invention provides an eye shield with at least one thin, soft, pliable air-filled cushion member or "pillow" of plastic material, sized and shaped to fit within the cavity formed by the orbital bone structure around the eye. The cushion member is held in place by the eye shield support removably affixed to the face of the patient. An adhesive layer may be placed on the cushion member for contact with the closed eyelid of the patient, to assist in holding the eyelid closed, and to assist in keeping the cushion member in place.

The cushion member has a pleated, folded, or grooved perimeter wall or side edge joining the pillow surfaces to allow expansion of air in a "bellows" effect at the perimeter of the cavity when pressure is applied. Thus, any direct pressure on the central part of the eye globes is redistributed peripherally to relieve, protect, and cushion the eye. Since the air cavity contains air at atmospheric pressure the expansion and cushioning effect is a function of the surface area of the air chamber and the elasticity and flexibility of the material. According to the invention, this grooving, indentation, pleating, or folding at the side edges permits increase of the surface area for the soft cushioning effect. A feature and advantage of the invention is that the air in the cushion or pillow is only at atmospheric pressure to achieve the desired soft cushioning and protection of the eye.

The invention also provides a central depression for accommodating the curvature of the eye globe.

BRIEF DESCRIPTION OF THE DRAWINGS

FIG. 7 is plan view of the eye shield of FIGS. 1-3 applied to the face of a patient.

DESCRIPTION OF PREFERRED EXAMPLE EMBODIMENTS AND BEST MODE OF THE INVENTION

Figure 1:
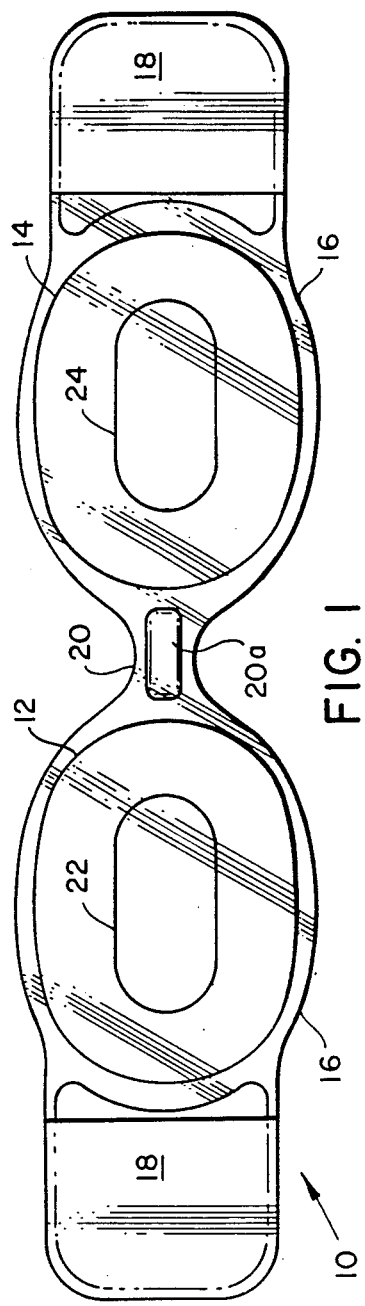
FIG. 1 is a plan view from above of an eye shield device according to the present invention.
Figure 2:
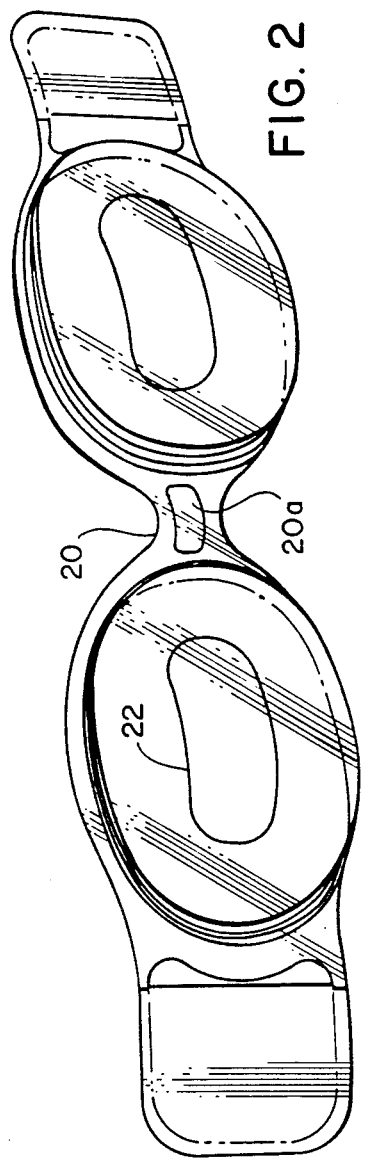
FIG. 2 is a perspective view of the eye shield of FIG. 1.
Figure 3:
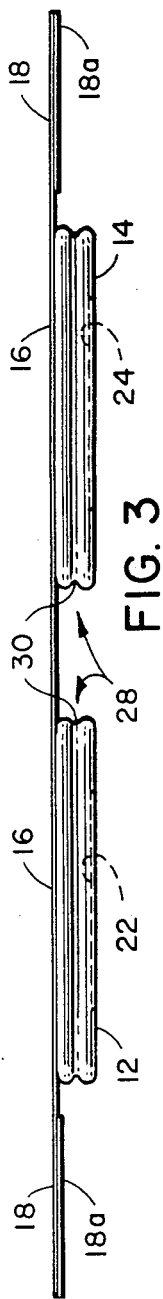
FIG. 3 is a side view of the eye shield device of the present invention.

A preferred embodiment of the eye shield device 10 of the present invention is illustrated in FIGS. 1-3. As seen in FIGS. 1-3, spaced-apart air-filled cushion members or pillows 12 and 14 are formed on the inner surface of eye shield support 16. During use, the cushion members or pillow 12 and 14 are positioned upon the closed eyes of an individual. The eye shield 10 is secured in place by adhesive tabs 18 which are applied at the temples. The cushion members 12 and 14 and support 16 may be transparent for visual confirmation of the closed state of the eyelids during application of the eye shield.

Cushion members 12 and 14 preferably comprise soft, pliable air-filled pillows of thin plastic material, for example a non-toxic, non-irritating medical grade PVC. The cushion members or pillows form an air cavity approximately one centimeter thick. The eye shield support 16 of FIGS. 1-3 is approximately twenty centimeters long, with end portion tabs 18 which are adhesively and removably affixed to the head of the individual just below the temple areas. The center connecting portion 20 which lies over the bridge of the nose may be reinforced, for example with reinforcing rib 20a.

The cushions 12 and 14 are formed on the inside or undersurface of the eye shield facing the eyes of a patient with central cavities or indentations 22 and 24 to accommodate the protruding curvature of the eyeballs or eye globes. The support member 16 to which the cushion members or pillows are bonded actually forms the outside or top surface of the cushion members 12 and 14. The eye shield 10 therefore comprises an integral device.

The two-cushion eye shield device shown in FIGS. 1–3 may be quickly and readily applied to a patient in a simple operation that requires but a single step and provides a reliable, inexpensive means for protecting the eye of the patient. The adhesive tabs 18 may be covered with pull off strips 18a which are removed prior to application.

Figure 5A:
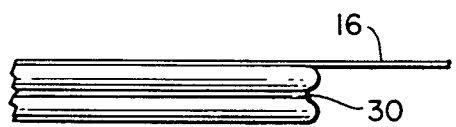
FIGS. 5A and 5B are fragmentary side views showing the edge or perimeter of a cushion member or pillow in expanded conditions respectively.
Figure 5B:
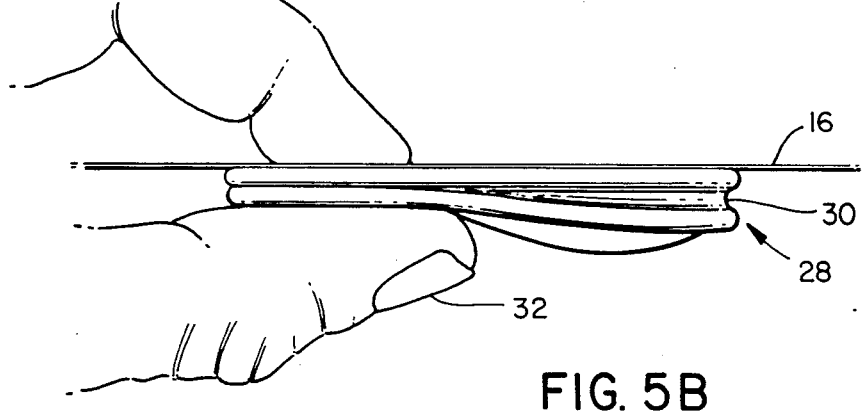

As shown in FIG. 3 and FIGS. 5A and 5B, the perimeter wall 28 connecting top and bottom surfaces or flat faces of the cushion members or pillows 12 and 14 is formed with at least one pleat, groove or fold 30 for expansion of air in a bellows effect at the perimeter if pressure is applied on the central portions of the eye. Air pressure is thus redistributed peripherally as shown in FIG. 5B where an object, for example a thumb 32 is applying pressure at the center of the pillow.

Figure 4:
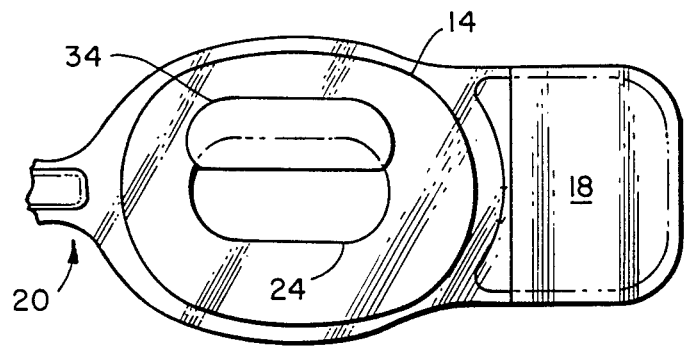
FIG. 4 is a fragmentary plan view from below of an alternative eye shield device according to the present invention showing an adhesive layer to be applied against the eyelid.

In FIG. 4 there is depicted adhesive layer 34 applied to the upper portion of the side of the cushion member 14 that will contact the upper eyelid of the closed eye of the individual. Adhesive layer 34 contacts the closed eyelid thereby securing the cushion member in place and at the same time helping to keep the eye closed.

Figure 6:
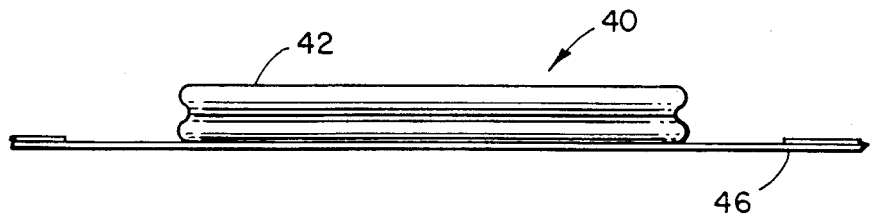
FIG. 6 is a side view of a single cushion member eye shield with the single pillow applied on adhesive tape.

Turning to FIG. 6, there is depicted an eye shield 40 comprising a single air-filled cushion member 42 according to the present invention. In some circumstances it may be preferable to employ a single cushion member, for example, if it is desired to close and protect one eye of a patient while the other eye is being treated. Furthermore, the single cushion member may be backed by a strip of adhesive tape 46 for removable affixation to the bridge of the nose an one temple area of the face. In this example, the cushion member or pillow 42 is formed as a single unit with integral upper and lower faces or surfaces, one of which adheres to the adhesive strip 46.

In FIG. 7, the eyeshield of FIGS. 1–3 is applied to the face of a patient with upper eyelids closed and the cushions seated appropriately in the orbital cavities.

It is contemplated that the cushion members or pillows of the present invention may be utilized with other support means to hold the members in place. For example, a mask device that ties around the head of the patient or at the back of the head such as described in U.S. Pat. Nos. 4,019,516 and 1,886,725 may be employed. Or a flexible band or strip of cloth may encircle the head to hold the cushion members or pillows in place.

While the invention has been described with reference to particular example embodiments, it is intended to cover all modifications and equivalents within the scope of the following claims.

I claim:

1. A device for protecting an individual's eye comprising a soft, pliable air-filled thin plastic pillow, constructed and arranged to rest on the closed eye inside the orbital bone of the individual, and substantially fill the cavity formed by the orbital bone structure around the eye, and securing means to removably hold said pillow upon the closed eye of the individual, said pillow comprising a top layer and a bottom layer spaced apart substantially in parallel, and a perimeter wall integrally connecting said top and bottom layers, said perimeter wall being formed with at least one flexible longitudinal folded pleat entirely around the perimeter for expansion and contraction of the pillow at the perimeter, said pillow being air filled at substantially atmospheric pressure for maintaining the eyelids closed with soft cushioning pressure.

2. The device of claim 1 wherein the surface of the pillow adapted to be adjacent the individual's eye comprises a central depression for accommodating the curvature of the eye globe.

3. An eye shield device comprising a support member having an inner surface, a pair of spaced-apart soft, pliable air-filled cushion members affixed to said inner surface of said support member, said cushion members being constructed and arranged to rest on the closed eyes inside the orbital bones of an individual and fill substantially the cavities formed by the orbital bone structure around the eyes of said individual, and securing means for removably affixing said support member to the head of said individual to hold said cushion members in position upon the closed eyes of the individual, said cushion members comprising a top layer and a bottom layer spaced apart and substantially in parallel, and a perimeter wall integrally connecting said top and bottom layers, said perimeter wall being formed with at least one flexible longitudinal folded pleat entirely around the perimeter for expansion and contraction of the pillow at the perimeter, said cushion members being thin plastic pillows air-filled at substantially atmospheric pressure for maintaining the eyelids closed with soft cushioning pressure.

4. The eye shield device of claim 3 wherein said support member and said securing means comprises a supporting strip of adhesive tape.

5. The eye shield device of claim 3 further comprising adhesive means located on each of said cushion members to contact each eyelid of the individual to secure the cushion members on the eyelids.

6. The eye shield device of claim 3 wherein the surface of each of the cushion members adapted to be adjacent one of the individual's eyes comprises a central cavity for accommodating the curvature of the eye globe.

* * * * *